United States Patent [19]

Butina et al.

[11] Patent Number: 4,876,267

[45] Date of Patent: Oct. 24, 1989

[54] 5-AMINOSULPHORYL SUBSTITUTED INDOLE DERIVATIVES

[75] Inventors: Darko Butina, Arlesey; Michael D. Dowle, Ware; David E. Bays, Ware; Colin F. Webb, Royston, all of England

[73] Assignee: Glaxo Group Limited, London, England

[21] Appl. No.: 66,498

[22] Filed: Jun. 26, 1987

[30] Foreign Application Priority Data

Jun. 26, 1986 [GB] United Kingdom ............... 8615599

[51] Int. Cl.⁴ .................... A61K 31/40; C07D 209/16
[52] U.S. Cl. .................................... 514/415; 548/504
[58] Field of Search ................... 548/504; 514/415

[56] References Cited

U.S. PATENT DOCUMENTS 3,472,870 10/1969 Larsen ............................ 548/504
4,636,521 1/1987 Coates ........................... 514/415
4,672,067 6/1987 Coats ............................. 514/415

OTHER PUBLICATIONS

Suvorov, Chem Abs. 61, 5596h (1964).
Graevskaya, Chem Abs. 93, 62001e (1977).
De Bellis, Chem Abs. 56, 11545d (1961).
Chemical Abstracts, Fujisawa Pharmaceutical Co., Ltd, vol. 65, p. 196, col. 13663 (f) (1966).

Primary Examiner—Mark L. Berch
Attorney, Agent, or Firm—Bacon & Thomas

[57] ABSTRACT

Indole derivatives are disclosed of the formula (I):

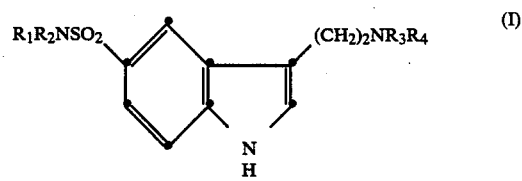

wherein $R_1$ represents H, or $C_{1-6}$ alkyl or $C_{3-6}$ Alkenyl;

$R_2$ represents a H, $C_{1-3}$ alkyl, $C_{3-6}$ alkenyl or $C_{5-7}$ cycloalkyl, or a phenyl or phen($C_{1-4}$)alkyl group in which the phenyl ring is optionally substituted by halogen or $C_{1-3}$ alkyl, $C_{1-3}$ alkoxy or hydroxyl, or by a group $NR^aR^b$, or $CONR^aR^b$, wherein $R^a$ and $R^b$ each independently represents H or $C_{1-3}$ alkyl;

$R_3$ and $R_4$, each independently represents H or $C_{1-3}$ alkyl or 2-propenyl;

and physiologically acceptable salts and solvates (e.g. hydrates) thereof.

The compounds have potent and selective vasoconstrictor activity and are indicated as useful for the treatment of migraine. The compounds may be formulated as pharmaceutical compositions with pharmaceutically acceptable carriers or excipients for administration by any suitable means. Various methods for the preparation of the compounds are disclosed.

2 Claims, No Drawings

5-AMINOSULPHORYL SUBSTITUTED INDOLE DERIVATIVES

This invention relates to indole derivatives, to processes for their preparation, to pharmaceutical compositions containing them and to their medical use, in particular to compounds and compositions of use in the treatment of migraine.

The pain of migraine is associated with excessive dilatation of the cranial vasculature, and known treatments for migraine include the administration of compounds having vasoconstrictor properties, such as ergotamine. However, ergotamine is a non-selective vasoconstrictor which constricts blood vessels throughout the body and has undesirable and dangerous side effects. Migraine may also be treated by administering an analgesic, usually in combination with an antiemetic, but such treatments are of limited value.

There is thus a need for a safe and effective drug for the treatment of migraine, which can be used either prophylactically or to alleviate an established headache, and a compound having a selective vasoconstrictor activity would fulfil such a role.

A number of classes of compounds having selective vasoconstrictor activity have been described.

In UK Patent Specification No. 2124210, a wide variety of indole derivatives are disclosed in which the indole 5-position substituent is a sulphonamidomethyl group which may optionally be substituted at the nitrogen atom by an alkyl, alkenyl, aryl, aralkyl or cycloalkyl group. As indicated in UK Patent Specification No. 2123210, these compounds selectively constrict the carotid arterial bed of the anaesthetised dog and are thus potentially useful for the treatment of migraine.

Indole derivatives containing a $C_{2-5}$ alkyl-sulphonamide group at the indole 5-position which have selective vasoconstrictor activity are described in UK Published Patent application No. 2150932. The nitrogen atom of the sulphonamide group may be substituted by a large number of groups including a phenyl or phen($C_{1-4}$)alkyl group.

European Published Patent Application No. 147107 describes indole derivatives having selective vasoconstrictor activity of formula:

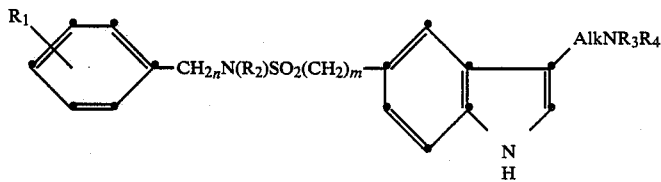

wherein $R_1$ represents a halogen atom or an alkyl, alkoxy or hydroxy group, or a group $NR_aR_b$ or $CONR_aR_b$, where $R_a$ and $R_b$, which may be the same or different, each represents a hydrogen atom or an alkly or alkenyl group, or together with the nitrogen atom to which they are attached $R_a$ and $R_b$ form a saturated monocyclic 5 to 7-membered ring which may contain an additional heterofunction; $R_2$ represents a hydrogen atom or a $C_{1-3}$ alkyl group; $R_3$ and $R_4$, which may be the same or different, each represents a hydrogen atom or a $C_{1-3}$ alkyl or propenyl group or $R_3$ and $R_4$ together form an aralkylidene group; Alk represents an alkylene chain containing two or three carbon atoms which may be unsubstituted or substituted by not more than two $C_{1-3}$ alkyl groups; n and m, which may be the same or different each represents an integer from 1 to 4 or n may be zero; and their physiologically acceptable salts and solvates.

We have now found a novel group of indole derivatives having potent and selective vasoconstrictor activity.

Thus, the present invention provides an indole of the general formula (I):

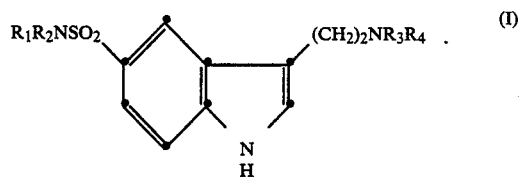

wherein
$R_1$ represents a hydrogen atom or a $C_{1-6}$ alkyl or $C_{3-6}$ alkenyl group;
$R_2$ represents a hydrogen atom, a $C_{1-3}$ alkyl, $C_{3-6}$ alkenyl or $C_{5-7}$ cycloalkyl group, or a phenyl or phen($C_{1-4}$) alkyl group in which the phenyl ring may be unsubstituted or substituted by a halogen atom or a $C_{1-3}$ alkyl, $C_{1-3}$ alkoxy or hydroxyl group, or by a group $NR^aR^b$, or $CONR^aR^b$, wherein $R^a$ and $R^b$, which may be the same or different, each represents a hydrogen atom or a $C_{1-3}$ alkyl group;
$R_3$ and $R_4$, which may be the same or different each represents a hydrogen atom or a $C_{1-3}$ alkyl or 2-propenyl group; and physiologically acceptable salts and solvates (e.g. hydrates) thereof.

It will be appreciated that the invention includes within its scope geometric isomers of compounds (I) and mixtures of such isomers.

Referring to the general formula (I), the alkyl groups and the alkyl moiety of the alkoxy groups may be straight chain or branched chain alkyl groups such as for example methyl, ethyl, propyl and isopropyl groups. The alkenyl groups preferably contain 3 or 4 carbon atoms, examples of which include propenyl and butenyl groups. The cycloalkyl groups preferably contain 5 or 6 carbon atoms and examples include cyclopentyl and cyclohexyl groups. When $R_2$ represents a substituted phenyl or phen($C_{1-4}$)alkyl group the substituent may be in the ortho, meta or para positions.

A preferred class of compounds represented by the general formula (I) is that wherein $R_1$ represents a $C_{1-6}$ alkyl group, for example a methyl group, or more particularly a hydrogen atom.

Another preferred class of compounds of general formula (I) is that wherein $R_3$ and $R_4$, which may be the same or different, each represents a hydrogen atom or a $C_{1-3}$ alkyl group, for example a methyl or ethyl group.

In the compounds of general formula (I), $R_2$ preferably represents a hydrogen atom or more especially an unsubstituted or substituted phenyl or phen($C_{1-4}$)alkyl group. Where $R_2$ represents a substituted or unsubstituted phen($C_{1-4}$)alkyl group, this will preferably be a phenylmethyl or phenylethyl group.

When $R_2$ represents a phenyl or phen($C_{1-4}$)alkyl group in which the phenyl ring is substituted by a halogen atom, the substituent may be, for example, a fluorine, chlorine or bromine atom. A $C_{1-3}$ alkoxy substituent on a phenyl ring in a compound of general formula (I) may be, for example, a methoxy or ethoxy group. In the compounds of general formula (I) wherein $R_2$ represents a phenyl or phen($C_{1-4}$)alkyl group in which the phenyl ring is substituted by an $NR^aR^b$ or $CONR^aR^b$ group, $R^a$ and $R^b$, which may be the same or different each preferably represents a hydrogen atom or a methyl group.

Suitable substituents on the phenyl ring in compounds of general formula (I) include, for example, methoxy and ethoxy groups.

In the compounds of general formula (I) wherein $R_2$ represents a substituted phenyl or phen($C_{1-4}$)alkyl group, the substituent is preferably at the para position.

A particularly preferred group of compounds falling within the scope of general formula (I) is that wherein $R_1$ represents a hydrogen atom; $R_3$ and $R_4$, which may be the same or different, each represents a hydrogen atom or a methyl group; and $R_2$ represents a phenyl or phen(Chd 1-2)alkyl group which may be unsubstituted or substituted at the para position of the phenyl ring by a $C_{1-3}$ alkoxy group.

Particularly preferred compounds of general formula (I) falling within this group are those in which $R_2$ represents a phenyl or phenethyl group which may be substituted at the para position by a methoxy or ethoxy group.

Preferred compounds according to the invention include: 3-(2-Aminoethyl)-N-[2-(4-methoxyphenyl)ethyl]-1H-indole-5-sulphonamide; N-(4-Ethoxyphenyl)-3-[2-(methylamino)ethyl]-1H-indole-5-sulphonamide; and their physiologically acceptable salts and solvates (for example hydrates) thereof.

Suitable phisologically acceptable salts of the indoles of general formula (I) include acid addition salts formed with inorganic or organic acids, for example hydrochlorides, hydrobromides, sulphates, nitrates, oxalates, phosphates, tartrates, citrates, fumarates, maleates, succinates, and sulphonates e.g. mesylates. Other salts may be useful in the preparation of compounds of formula (I) e.g. creatinine sulphate adducts.

It will be appreciated that the invention extends to other physiologically acceptable equivalents of the compounds according to the invention, i.e. physiologically acceptable compounds which are converted in vivo into the parent compound. Examples of such equivalents include physilogically acceptable, metabolically labile N-acyl derivatives.

Compounds of the invention selectively constrict the carotid arterial bed of the anaesthetised dog, whilst having a negligible effect on blood pressure. The selective vasoconstrictor action of compounds of the invention has been demonstrated in vitro.

Compounds of the invention are useful in treating pain resulting from dilatation of the cranial vasculature, in particular migraine and cluster headache.

Accordingly, the invention also provides a pharmaceutical composition adapted for use in human medicine which comprises at least one compound of formula (I) or a physiologically acceptable salt or solvate (e.g. hydrate) thereof and formulated for administration by any convenient route. Such compositions may be formulated in conventional manner using one or more pharmaceutically acceptable carriers or excipients.

Thus the compounds according to the invention may be formulated for oral, buccal, parenteral or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl-p-hydroxybenzoates or sorbic acid). The liquid preparations may also contain conventional buffers, flavouring, colouring and sweetening agents as appropriate.

For buccal administration the compositions may take the form of tablets or lozenges formulated in conventional manner.

The compounds of the invention may be formulated for parenteral administration by injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents, and/or agents to adjust the tonicity of the solution. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

For administration by inhalation the compounds according to the invention are conveniently delivered in the form of an aerosol spray presentation from pressurised packs, with the use of a suitable propellant, e.g. dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

A proposed dose of the compounds of the invention for oral, parenteral, buccal or rectal administration to man (of average bodyweight e.g. about 70 kg) for the treatment of migraine is 0.1 to 100 mg of the active ingredient per unit dose which could be administered, for example, up to 8 times per day, more usually 1 to 4 times per day. It will be appreciated that it may be necessary to make routine variations to the dosage depending on the age and weight of the patient as well as the severity of the condition to be treated.

For oral administration a unit dose will preferably contain from 0.5 to 50 mg e.g. 2 to 40 mg of the active ingredient. A unit dose for parenteral administration will preferably contain 0.2 to 5 mg of the active ingredient.

Aerosol formulations are preferably arranged so that each metered dose or 'puff' delivered from a pressurized aerosol contains 0.2 to 2 mg of a compound of the invention and each dose administered via capsules or cartridges in an inhaler or insufflator contains 0.2 to 20 mg. The overall daily dose by inhalation will be within the range 1 mg to 100 mg. Administration may be several times daily, for example from 2 to 8 times, giving for example 1, 2 or 3 doses each time.

The compounds of the invention may, if desired, be administered in combination with one or more other therapeutic agents, such as analgesics, anti-inflammatory agents and anti-nauseants.

According to another aspect of the invention, compounds of formula (I), and physiologically acceptable salts or solvates (e.g. hydrates) thereof, may be prepared by the general methods outlined below. In the following processes, $R_1$, $R_2$, $R_3$, and $R_4$ are as defined for the general formula (I) unless otherwise specified.

According to one general process (A), a compound of formula (I) may be prepared by the cyclisation of a compound of general formula (II):

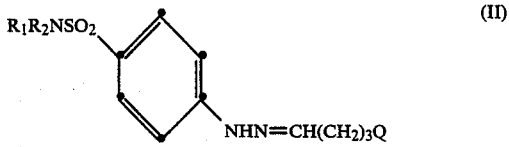

(II)

wherein Q is the group $NR_3R_4$ (or a protected derivative thereof) or a leaving atom or group such as a halogen atom (e.g. chlorine or bromine) or an acyloxy group (e.g. a carboxylic or sulphonic acyloxy group such as an acetoxy, chloroacetoxy, dichloroacetoxy, trifluoroacetoxy, p-nitrobenzoyloxy, p-toluenesulphonyloxy or methanesulphonyloxy group).

The reaction may conveniently be effected in aqueous or non-aqueous reaction media, and at temperatures of from 20° to 200° C., preferably 50° to 125° C.

Particularly convenient embodiments of the general process (A) are described below.

When Q is the group $NR_3R_4$ (or a protected derivative thereof) the process is desirably carried out in the presence of polyphosphate ester in a reaction medium which may comprise one or more organic solvents, preferably halogenated hydrocarbons such as chloroform, dichloromethane, dichloroethane, dichlorodifluoromethane, or mixtures thereof. Polyphosphate ester is a mixture of esters which may be prepared from phosphorus pentoxide, diethylether and chloroform according to the method described in 'Reagents for Organic Synthesis', (Fieser and Fieser, John Wiley and Sons 1967).

Alternatively the cyclisation may be carried out in an aqueous or non-aqueous reaction medium, in the presence of an acid catalyst. When an aqueous medium is employed this may be an aqueous organic solvent such as an aqueous alcohol (e.g. methanol, ethanol or isopropanol) or an aqueous ether (e.g. dioxan or tetrahydrofuran) as well as mixtures of such solvents, and the acid catalyst may be for example, an inorganic acid such as concentrated hydrochloric or sulphuric acid or an organic acid, such as acetic acid. (In some cases the acid catalyst may also act as the reaction solvent). In an anhydrous reaction medium, which may comprise one or more ethers (e.g. as preivously described) or esters (e.g. ethyl acetate), the acid catalyst will generally be a Lewis acid such as boron trifluoride, zinc chloride or magnesium chloride.

When Q is a leaving group such as a chlorine or bromine atom the reaction may be affected in an aqueous organic solvent, such as an aqueous alcohol (e.g. methanol, ethanol or isopropanol) or an aqueous ether (e.g. dioxan or tetrahydrofuran) in the absence of an acid catalyst, conveniently at a temperature of from 20° to 200° C., preferably 50° to 125° C. This process results in the formation of a compound of formula (I) wherein $R_3$ and $R_4$ are both hydrogen atoms.

According to a particular embodiment of general process (A) compounds of formula (I) may be prepared directly by the reaction of a compound of general formula (III):

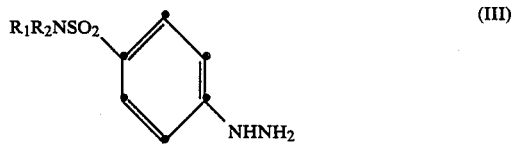

(III)

or a salt thereof, with a compound of formula (IV):

$$OHC(CH_2)_3Q \qquad (IV)$$

(wherein Q is as defined above) or a slat or protected derivative thereof (such as an acetal or ketal e.g. formed with an appropriate alkyl orthoformate or diol, or protected as a bisulphite addition complex) using the appropriate conditions as described above for the cyclisation of compounds of general formula (II). It will be appreciated that in this embodiment of the cyclisation process (A) a compound of general formula (II) is formed as an intermediate, and may be reacted in situ to form the desired compound of general formula (I).

Compounds of general formula (II) may, if desired, be isolated as intermediates during the process for the preparation of compounds of formula (I) wherein a compound of formula (III), or a salt or protected derivative thereof, is reacted with a compound of formula (IV), or a salt or protected derivative thereof, in a suitable solvent, such as an aqueous alcohol (e.g. methanol) at a temperature of, for example, 20° to 30° C. If an acetal or ketal of a compound of formula (IV) is used, it may be necessary to carry out the reaction in the presence of an acid (for example, acetic or hydrochloric acid).

Compounds of general formula (III) may be prepared for example from the corresponding nitro compounds, using conventional procedures.

A further general process (B) for preparing compounds of general formula (I) involves reacting a compound of general formula (V):

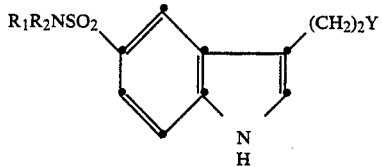

(wherein Y is a readily displaceable group) or a protected derivative thereof, with an amine of formula $R_3R_4NH$.

The displacement reaction may conveniently be carried out on those compounds of formula (V) wherein the substituent group Y is a halogen atom (e.g. chlorine, bromine or iodine) or a gorup $OR_5$ where $OR_5$ is, for example, an acyloxy group which may be derived from a carboxylic or sulphonic acid, such as an acetoxy, chloroacetoxy, dichloroacetoxy, trifluoroacetoxy, p-nitrobenzoyloxy, p-toluenesulphonyloxy or methanesulphonyloxy group.

The displacement reaction may be conveniently effected in an inert organic solvent (optionally in the presence of water), examples of which include alcohols, e.g. ethanol; cyclic ethers, e.g. dioxan or tetrahydrofuran; acylic ethers e.g. diethylether; esters, e.g. ethyl acetate; amides, e.g. N,N-dimethylformamide; and ketones e.g. acetone or methylethyl ketone, at a temperature of from $-10°$ to $+150°$ C., preferably 20° to 50° C.

The compounds of general formula (V) wherein Y is a halogen atom may be prepared by reacting a hydrazine of general formula (III) with an aldehyde or ketone (or a protected derivative thereof) of formula (IV) in which Q is a halogen atom, in an aqueous alkanol (e.g. methanol) containing an acid (e.g. acetic or hydrochloric acid). Compounds of formula (V) wherein Y is the group $OR_5$ may be prepared from the corresponding compound wherein Y is a hydroxyl group by acylation or sulphonylation with the appropriate activated species (e.g. anhydride or sulphonyl chloride) using conventional techniques. The intermediate alcohol may be prepared by cyclisation of a compound of formula (II) wherein Q is a hydroxyl group (or a protected derivative thereof) under standard conditions.

Compounds of formula (I) may also be prepared by another general process (C) involving reduction of a compound of general formula (VI):

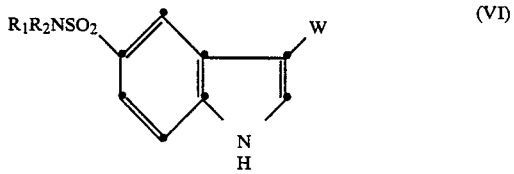

(wherein W is a group capable of being reduced to give the required $-(CH_2)_2NR_3R_4$ group or to give a protected derivative of $-(CH_2)_2NR_3R_4)$ or a salt or protected derivative thereof.

The required $-(CH_2)_2-$ and $-NR_3R_4$ groups at the 3-position may be formed by reduction steps which take place separately or together in any appropriate manner.

Examples of groups represented by the substituent W include $-(CH_2)_2NO_2$; $-CH=CHNO_2$; $-(CH_2)_2N_3$; $-CH_2CN$; $-CH_2CHO$; $-COCH_2Z$; $-CH_2CH=NOH$; $-(CH_2)_2NR_3COR_4'$; $-COCONR_3R_4$; $-CH_2COZ$ and $-CH(OH)CH_2NR_3R_4$; (wherein Z is an azido group or the group $-NR_3R_4$ or a protected derivative thereof and $R_4$ is a hydrogen atom or a methyl or ethyl group, or $R_4'$ represents the group $OR_6$, and $R_6$ is an alkyl or aralkyl group).

Groups which may be reduced in the $-(CH_2)_2-$ moiety at the 3-position include the corresponding unsaturated groups and corresponding groups containing a hydroxyl group or a carbonyl function.

Groups which may be reduced to the group $-NR_3R_4$ where $R_3$ and $R_4$ are both hydrogen include nitro, azido, hydroxyimino and nitrile groups. In the latter case, reduction yields the group $-CH_2NH_2$ and thus provides a methylene group of the $-(CH_2)_2-$ moiety.

The required $-NR_3R_4$ group wherein $R_3$ and/or $R_4$ are other than hydrogen may be prepared by reduction of a nitrile $-CH_2CN$ or an aldehyde $-CH_2CHO$ in the presence of an amine, $R_3R_4NH$.

A particularly suitable method for preparing a compound of formula (I) wherein $R_3$ and/or $R_4$ is other than hydrogen is reductive alkylation of the corresponding compound wherein $R_3$ and/or $R_4$ represent hydrogen with an appropriate aldehyde or ketone (e.g. formaldehyde or acetone) in the presence of a suitable reducing agent. In some instances (e.g. for the introduction of the group(s) $R_3$ and/or $R_4$ where these represent methyl) the aldehyde (e.g. formaldehyde) may be condensed with the amine and the intermediate thus formed may subsequently be reduced using a suitable reducing agent. The required $-NR_3R_4$ group wherein $R_3$ and/or $R_4$ are other than hydrogen may also be prepared by reduction of a corresponding acylamino group e.g. of the formula $-(CH_2)_2NR_3COR_4'$, where $R_4'$ is as previously defined.

It will be appreciated that the choice of reducing agent and reaction conditions will be dependent on the nature of the group W, as well as the other groups already present on the molecule.

Suitable reducing agents which may be used in the above process for the reduction of compounds of formula (VI) wherein W represents, for example, the groups $-(CH_2)_2NO_2$, $-CH=CHNO_2$, $-(CH_2)_2N_3$, $-CH_2CN$, $-CH_2CH=NOH$ and $-CH(OH)CH_2NR_3R_4$ include hydrogen in the presence of a metal catalyst, for example Raney Nickel or a noble metal catalyst such as platinum, plastinum oxide, palladium, palladium oxide or rhodium, which may be supported, for example, on charcoal, kieselguhr or alumina. In the case of Raney Nickel, hydrazine may also be used as the source of hydrogen. This process may conveniently be carried out in a solvent such as an alcohol e.g. ethanol, an ether, e.g. dioxan or tetrahydrofuran, an amide, e.g. dimethylformamide or an ester e.g. ethyl acetate, and at a temperature of from $-10°$ to $+50°$ C., preferably $-5°$ to $+30°$ C.

The reduction process may also be affected on compounds of formula (VI) wherein W represents, for example, the groups $-(CH_2)_2NO_2$, $-CH=CHNO_2$, $-(CH_2)_2N_3$, $-CH(OH)CH_2NR_3R_4$ or $-COCH_2Z$ (where Z is as previously defined), using an alkali metal or alkaline earth metal borohydride or cyanoborohydride e.g. sodium or calcium bobohydride or cyanoborohydride which process may conveniently be carried out in an alcohol such as propanol or ethanol, or a nitrile such as acetonitrile, and at a temperature of from 10° to 100° C., preferably 50° to 100° C. In some instances the reduction using a borohydride may be carried out in the presence of cobaltous chloride.

Reductive alkylation of a compound of formula (VI) may be effected using an alkali metal or alkaline earth metal borohydride or cyanoborohydride. The reaction may be effected in an aqueous or nonaqueous reaction medium, conveniently in an alcohol (e.g. methanol or ethanol) or an ether (e.g. dioxan or tetrahydrofuran) optionally in the presence of water. The reaction may conveniently be carried out at a temperture in the range 0° to 100° C., preferably 5° to 50° C.

Compounds of formula (VI) wherein W represents, for example, $-(CH_2)_2NO_2$; $-CH=CHNO_2$; $-(CH_2)_2N_3$; $-(CH_2)_2NR_3COR_4$; $-CH_2CH=NOH$; $-CH(OH)CH_2NR_3R_4$; $-COCONR_3R_4$; $-CH_2COZ$ or $-COCH_2Z$ (where $R_4'$ and Z are as previously defined) may also be carried out using a metal hydride such as lithium aluminium hydride. This reaction may be carried out in a solvent, for example as ether such as tetrahydrofuran, and conveniently at a temperature in the range $-10°$ to $+100°$ C., preferably 50° to 100° C.

A particular embodiment of general process (C) is the reduction of a compound of formula (VI) wherein W is the group $-CH_2CN$, for example by catalytic reduction with hydrogen in the presence of a catalyst such as palladium on charcoal or rhodium on alumina, optionally in the presence of an amine $HNR_3R_4$. The reduction may be effected in a suitable solvent such as an alcohol e.g. methanol or ethanol.

A compound of general formula (I) where $R_4$, is a hydrogen atom may also be prepared by hydrogenolysis of a corresponding compound wherein $R_4$ is a benzyl group, e.g. with hydrogen in the presence of a catalyst, e.g. 10% palladium on carbon.

The starting materials or intermediate compounds of formula (VI) wherein W represents $-(CH_2)_2NO_2$, $-CH=CHNO_2$, $-CH_2CN$ or $-COCH_2Z$ may be prepred by analogous methods to those described in UK Patent Specification No. 2035310, and 'A Chemistry of Heterocyclic Compounds—Indoles Part II', Chapter VI, edited by W J Houlihan (1972) Wiley Interscience, New York.

Compounds of formula (VI), wherein W is the group $-CH_2CHO$ may be prepared by oxidation (e.g. with Jones' reagent) or a compound of formula (V) wherein Y is a hydroxyl group. A compounds of formula (VI) wherein W is the group $-CH_2CH=NOH$ may be prepared by treatment of the corresponding aldehyde with hydroxylamine hydrochloride using standard conditions.

The intermediate compound of formula (VI) wherein W is the group $-(CH_2)_2N_3$ may be prepared from a compound of formula (V) hwerein Y is a halogen atom using standard procedures.

Standard reducing agents such as sodium bobohydride may be used to prepare a compound of formula (VI) wherein W is the group $-CH(OH)CH_2NR_3R_4$ from the corresponding compoun of formula (VI) wherein W is thre group $-COCH_2NR_3R_4$.

A compound of formula (VI) wherein X is the group $-(CH_2)_2NR_3COR_4$ may be prepared by acylation of the corresponding unsubstituted amine using conventional procedures.

According to a further general process (D) a compound of formula (I) according to the invention, or a slat or protected derivative thereof, may be converted into another compound of formula (I) using conventional procedures.

For example, a compound of general formula (I) wherein one or more of $R_1$, $R_2$, $R_3$ and $R_4$ are alkyl groups may be prepared from the corresponding compounds of formula (I) wherein one or more of $R_1$, $R_2$, $R_3$ and $R_4$ represent hydrogen atoms, by reaction with a suitable alkylating agent such as a compound of formula $R_xL$, (where $R_x$ represents the desired $R_1$, $R_2$, $R_3$ and $R_4$ group and L represents a leaving group such as a halogen atom or a tosylate group) or a sulphate $(R_x)_2SO_4$. Thus, the alkylating agent may be for example an alkyl halide (e.g. methyl or ethyl iodide), alkyl tosylate (e.g. methyl tosylate) or dialkysulphate (e.g. dimethylsulphate).

The alkylation reaction may conveniently be carried out in an inert organic solvent such as an amide (e.g. dimethylformamide), an ether (e.g. tetrahydrofuran) or an aromatic hydrocarbon (e.g. toluene) preferably in the presence of a base. Suitable bases include, for example, alkali metal hydrides such as sodium or potassium hydride; alkali metal amides such as sodium amide; alkali metal carbonates such as sodium carbonate; a;kali metal alkoxides such as sodium or potassium methoxide, ethoxide or t-butoxide; and tetrabutylammonium fluoride. When an alkyl halide is employed as the alkylating agent the reaction may also be carried out in the presence of an acid scavenging agent such as propylene or ethylene oxide. The reaction may be conveniently effected at a temperature of from $-20°$ to 100° C.

Compounds of formula (I) wherein one or both of $R_3$ and $R_4$ represents propenyl may be prepared similarly, using an appropriate compound of formula $R_xL$ or $(R_x)_2SO_4$.

According to another general process (E), a compound of general formula (I) according to the invention, or a salt thereof may be prepared by subjecting a protected derivative of general formula (I) or a salt thereof to reaction to remove the protecting group or groups.

Thus, at an earlier stage in the reaction sequence for the preparation of a compound of general formula (I) or a salt thereof it may have been necessary or desirable to protect one or more sensitive groups in the molecule to avoid undesirable side reactions. For example it may be necessary to protect the group $NR_3R_4$, wherein $R_3$ and/or $R_4$ represents hydrogen, by protonation or with a group easily removable at the end of the reaction sequence. Such groups may include, for example, aralkyl groups, such as benzyl, dipheylmethyl or triphenylmethyl; or acyl groups such as N-benzyloxycarbonyl, t-butoxycarbonyl or phthaloxyl.

In some cases, it may also be desirable to protect the indole nitrogen with, for example, an aralkyl group such as benzyl.

Subsequent cleavage of the protecting group or groups may be achieved by conventional procedures. Thus, an aralkyl group such as benzyl, may be cleaved by hydrogenolysis in the presence of a catalyst (e.g. palladium on charcoal) or sodium and liquid ammonia; an acyl group such as N-benzyloxycarbonyl may be removed by hydrolysis with, for example, hydrogen bromide in acetic acid or by reduction, for example by catalytic hydrogenation. The phthaloyl group may be removed by hydrazinolysis (e.g. by treatment with hydrazine hydrate) or by treatment with a primary amine (e.g. methylamine).

As will be appreciated, in some of the general processes (A) to (D) described previously it may be necessary or desirable to protect any sensitive groups in the molecule as just described. Thus, a reaction step involivng deprotection of a protected derivative of general formula (I) or a slat thereof may be carried out subsequent to any of the previously described processes (A) to (D).

Thus, according to a further aspect of the invention, the following reactions in any appropriate sequence may if necessary and/or desired be carried out subsequent to any of the processes (A) to (D):

(i) removal of any protecting groups; and
(ii) conversion of a compound of general formula (I) or a salt thereof into a physiologically acceptable salt or solvate (e.g. hydrate) thereof.

Where it is desired to isolate a compound of the invention as a salt, for example as an acid addition salt, this may be achieved by treating the free base of general formula (I), with an appropriate acid, preferably with an equivalent amount, or with creatinine sulphate in a suitable solvent (e.g. aqueous ethanol).

The starting materials or intermediate compounds for the preparation of the compounds according to this invention may be prepared by analogous methods to those described in UK Patent Specification Nos. 2035310 and 2124210.

As well as being employed as the last main step in the preparative sequence, the general methods indicated above for the preparation of the compounds of the invention may also be used for the introduction of the desired groups at an intermediate stage in the preparation of the required compound. Thus, for example, the required group at the 5-position may be introduced before or after cyclisation to form the indole nucleus. It should therefore be appreciated that in such multi-stage processes, the sequence of reactions should be chosen in order that the reaction conditions do not affect groups present in the molecule which are desired in the final products.

The invention is further illustrated by the following Examples. All temperatures are in °C.

Chromatography was carried out in the conventional manner using Silica gel (Merck, Kieselgel 60, Art. 7734) or by flash chromatography on silica (Merck 9385) and thin layer chromatography (t.l.c.) on silica (Macherly-Nagel, Polygram) except where otherwise indicated.

EXAMPLE 1

3-(2-Aminoethyl)-1H-indole-5-sulphonamide, compound with creatinine sulphate and water 1:1:2

(i)
4-[2-([4-(1,3-Dihydro-1,3-dioxo-2H-isoindol-2-yl)butylidene]hydrazino]benzenesulphonamide A solution of 4-hydrazinobenzenesulphonamide (7.5g) in 25% aqueous acetic acid (500 ml) was added to phthalimidobutyraldehyde diethyl acetal (11.7 g). The mixture was stirred on a steam bath for 2 h and cooled to room temperature. Filtration and washing with boiling methanol (200 ml) gave the product as a crystalline solid (9.4 g) m.p. 191°–194°.

(ii)
3-[2-(1,3-Dihydro-1,3-dioxo-2H-isoindol-2-yl)ethyl]-1H-indole-5-sulphonamide The produce of stage (i) (5.0 g) was added to a solution of polyphosphate ester (25 g) in chloroform (50 ml) and the mixture was heated at reflux for 25 min. The reaction was cooled and the chloroform evaporated, the residue was stirred with iced water (100 g) for 1 h and the resultant solid was collected and washed with water (4.1 g). The product was recrystallised by adding dimethylformamide to a refluxing mixture of the product in methanol (200 ml) until a clear solution was obtained. Water (100 ml) was then added, precipitated impurities were filtered off and the filtrate evaporated to remove methanol. The product precipitated as a solid which was dried to give the title compound m.p. 285°–290°. Assay found: C,58.1;H,4.3,N,11.4; $C_{18}N_{15}N_3O_3S$ requires C,58.5;H,4.1;N,11.4%.

(iii) 3-(2-Aminoethyl)-1H-indole-5-sulphonamide compound with creatinine sulphate and water (1:1:2)

To a suspension of the product of stage (ii) (1.85 g) in ethanol (74 OP, 30 ml) was added hydrazine hydrate (0.5 g). The mixture was stirred between 60° and 70° for 1.5 h and then cooled to room temperature. 2 N Hydrochloric acid was added and the mixture was warmed between 25° and 45° for 1 h. A precipitate was filtered off and the filtrate was basified with 2 N NaOH (30 ml). The solution was then evaporated, and the residue taken up with methanol. A solid was filtered off and the filtrate was filtered through a column of silica (TLC grade 60 g). Evaporation of the eluent gave a solid (1.2 g) which was dissolved in ethanol (50 ml). The solution was diluted with ether (150 ml) and filtered. The filtrate was then evaporated to a foam (0.45 g), which was dissolved in acetone (1 ml) and creatinine sulphate (0.32 g) in water (1 ml) was added. The resulting crystalline solid was filtered off and recrystallised from water to give the title compound as a solid (0.13 g) m.p. 252°–259°.

Assay found C,34.18;H,4,92;N,17.03. $C_{10}H_{13}N_3O_2S.C_4H_7N_3O.H_2SO_4.2H_2O$ requires C,34.56;H,5.39;N,17.27%.

EXAMPLE 2

3-(2-Aminoethyl)-N-[2-(4-methoxyphenyl)ethyl]-1H-indole-5-sulphonamide compound with creatinine, sulphuric acid and water (1:1:1:1)

(i)
N-[2-(4-Methoxyphenyl)ethyl]-4-nitrobenzenesulphonamide

4-Nitrobenzenesulphonyl chloride (10 g) was added portionwise to a stirred solution of 4-methoxyphenethylamine (6.8 g) in pyridine (40 ml) and the resulting solution stirred at room temperature for 30 min. The solution was partitioned between hydrochloric acid (5 N, 400 ml) and ethyl acetate (2×250 ml). The combined extracts were washed with hydrochloric acid (5 N, 100 ml), sodium bicarbonate (8%, 100 ml) dried —MgSO₄) and evaporated in vacuo to give an oil. The oil was purified by column chromatography eluted with hexane:ethyl acetate (2:1) to give the title compound as a solid (4.7 g) m.p. 92°–93°.

(ii)
4-Amino-N-[2-(4-methoxyphenyl)ethyl]benzenesulphonamide

A solution of the product of stage (i) (4.5 g) in ethanol (150 ml) was hydrogenated at room temperature and pressure over 10% palladium oxide on charcoal (50% aq. paste, 0.5 g) for 2 h until hydrogen uptake ceased (1000 ml). Chloroform (150 ml) was added, and the mixture stirred until the product dissolved. The catalyst was filtered off, washed with ethanol, and the filtrate evaporated in vacuo to give a solid (3.8 g). A sample (0.2 g) was purified by flash chormatography eluted with chloroform:methanol (50:1) to give the title compound as a solid (0.11 g). m.p. 144°–146°.

(iii)
4-Hydrazino-N-[2-(4-methoxyphenyl)ethyl]benzenesulphonamide hydrochloride.

A solution of sodium nitrite (0.8 g) in water (20 ml) was added dropwise to a stirred suspension of the product of stage (ii) (3.5 g) in a mixture of concentrated hydrochloric acid (100 ml) and water (100 ml) keeping the temperature below −5° C. The resulting solution was stirred at about −5° C. for 30 min, when a solution of tin (II) chloride dihydrate (13 g) in concentrated hydrochloric acid (100 ml) was added. The resulting suspension was allowed to warm to room temperature over 1 h. The solid was filtered off, washed with ether, and dried in vacuo to give a solid (3.0 g). A sample (2 g) was crystallised from a mixture of methanol and isopropyl acetate to give the title compound as a solid (0.9 g) m.p. 208°–209°.

(iv)
3-(2-Aminoethyl)-N-[2-(4-methoxyphenyl)ethyl]-1H-indole-5-sulphonamide compound with creatinine, sulphuric acid, and water (1:1:1:1)

A solution of the product of stage (iii) (1.0 g) in a mixture of ethanol (90 ml) and water (10 ml) containing 4-chlorobutanal, dimethyl acetal (0.4 ml) was heated at reflux for 18 h, cooled, and evaporated in vacuo to give an oil which was purified by flash chromatography eluted with dichloromethane:ethanol:aqueous ammonia (25:8:1) to give the title compound free base as an oil (0.13 g). The oil was dissolved in a hot mixture of ethanol (9 ml) and water (1 ml) and an aqueous solution of creatinine and sulphuric acid (1:1, 2M, 0.2 ml) added. Filtration of the cooled mixture gave the title compound as a solid (0.17 g) m.p. 174°–177°.

T.l.c. Silica:Dichloromethane-ethanol-aqueous ammonia (25:8:1) det u.v.+IPA Rf=0.4.
Analysis found: C,45.9;H,5.6;N,13.5. $C_{19}H_{23}N_3O_6S \cdot C_4H_7N_3O \cdot H_2SO_4 \cdot H_2O$ required C,45.8;H,5.7;N,13.9%.

EXAMPLE 3

3[2-(Dimethylamino)ethyl]-N-[2-(4-methoxyphenyl)ethyl]-1H-indole-5-sulphonamide oxalate hydrate Aqueous formaldehyde (40% w/v, 0.75 ml) was added dropwise to a stirred solution of the product of Example 2, as the free base (0.7 g) in n-propanol (20 ml) at 0° C., and the resulting solution stirred at 0° C. for 30 min. Sodium borohydride (0.76 g) was added, and the mixture stirred at 0° C. for 2 h. Hydrochloric acid (2 N, 50 ml) was added, the resulting solution basified (Na$_2$CO$_3$) and extracted with ethyl acetate (2×75 ml). The combined extracts were dried (Na$_2$SO$_4$) and evaporated in vacuo to give an oil which was purified by flash chromatography eluted with dichloromethane:ethanol:ammonia (50:8:1) to give pure title compound free base as an oil (0.2 g). This was dissolved in a solution of oxalic acid (0.032 g) in absolute ethanol (3 ml) and the salt precipitated by adding ethyl acetate (20 ml) and dry ether (100 ml). The salt was filtered off, and dried in vacuo to give the title compound as a solid (0.08 g) m.p. 187°–190°.

T.l.c. Silica:Dichloromethane-ethanol-aqueous ammonia solution (50:8:1) det u.v.+IPS Rf=0.3.
Analysis found: C,54.7;H,6.05;N,8.1. $C_{21}H_{27}N_3O_5S \cdot C_2H_2O_4 \cdot 0.8H_2O$ requires C,54.6;H,6.1;N,8.3%.

EXAMPLE 4

3-(2-Aminoethyl)-N-(4-ethoxyphenyl)-1H-indole-5-sulphonamide hydrochloride hydrate

(i)
4[2-[4-(1,3-Dihydro-1,3-dioxo-2H-isoindol-2-yl)butylidene]hydrazino]-N-(4-ethoxyphenyl)benzenesulphonamide A solution of 4-hydrazino-N-(4-ethoxyphenyl)benzenesulphonamide hydrochloride (1.2 g) in 25% aqueous acetic acid (100 ml) was added to phthalimidobutyraldehyde diethyl acetal (1 g). The resulting suspension was stirred at room temperature for 1 h, basified (sodium carbonate) and extracted with ethyl acetate (2×100 ml). The combined organic extracts were dried and evaporated in vacuo to give a solid which gave the title compound (1.5 g) on trituration with ethyl acetate, m.p. 156°–158°.

(ii)
3-[2-(1,3-Dihydro-1,3-dioxo-2H-isoindol-2-yl)ethyl]-N-(4-ethoxyphenyl)-1H-indole-5-sulphonamide A solution of the product of stage (i) (0.3 g) in chloroform (15 ml) containing polyphosphate ester (3 ml) was heated at reflux for 3 h, where upon a further portion of the ester solution (2 ml) was added. After a further 3 h, chloroform (10 ml) and ester (30 ml) were added, and the resulting mixture stirred at room temperature for 1 h. The resulting suspension was filtered to give the title compound as a solid (0.09 g) t.l.c. Silica:Diethylether det UV+Ce$^{IV}$Rf=0.45 (major) 0.5, 0.4 (minor).

(iii)
3-(2-Aminoethyl)-N-(4-ethoxyphenyl)-1H-indole-5-sulphonamide hydrochlodie hydrate (4:4:3)

A solution of the product of stage (ii) (1.7 g) in ethanol (100 ml) containing hydrazine hydrate (2 ml) was heated at reflux for 2 h, cooled and the solvent evaporated in vacuo. The residue was partitioned between sodium carbonate (2 N, 50 ml) and ethyl acetate (2×50 ml) and the combined organic extracts were dried (Na$_2$SO$_4$) and evaporated in vacuo to give an oil which was purified by flash chromatography eluted with dichlormethane:ethanol:ammonium hydroxide (20:5:0.2) to give the title compound free base an an oil. The oil was dissolved in methanol (10 ml) ethereal hydrogen chloride (3 ml) added, and the salt precipitated by the addition of excess dry ether (300 ml). The salt was filtered off and dried in vacuo to give the title compound as a solid (0.26 g) m.p. 130°–133°.
Analysis Found: C,52.9;H,5.7;N,10.0; $C_{18}H_{21}N_3O_3S \cdot HCl \cdot 0.75H_2O$ requires C,52.8;H,5.7;N,10.3%.

EXAMPLE 5

3-(2-Aminoethyl)-N-phenyl-1H-indole-5-sulphonamide maleate hydrate (4:4:1)

(i)
4[2-[4-(1,3-Dihydro-1,3-dioxo-2H-isoindol-2-yl)butylidene]hydrazino]-N-phenyl benzenesulphonamide Finely-divided phthalimidobutyraldehyde diethyl acetal (0.5 g) was added to a stirred solution of 4-hydrazino-N-phenyl-benzenesulphonamide (0.5 g) in 25% aqueous acetic acid (50 ml). After 30 min, the solution was basified (Na$_2$CO$_3$) and extracted with ethyl acetate (2×50 ml). The combined organic extracts were dried (MgSO$_4$) and evaporated in vacuo to give an oil which was purified by flash chromatography eluted with ether to give the title compound as a solid (0.3 g) m.p. 126°–129°.

(ii)
3-(2-Aminoethyl)-N-phenyl-1H-indole-5-sulphonamide maleate hydrate (4:4:1)

A solution of the product of stage (i) (5.08 g) in glacial acetic acid (40 ml) containing boron trifluoride, etherate (6.7 ml) was heated on a steam bath for 15 min, cooled, diluted with water (200 ml) basified (Na$_2$CO$_3$) and extracted with ethyl acetate (2×200 ml). The combined organic extracts were dried (MgSO$_4$) and evaporated in vacuo to give crude 3-[2-(1,3-dihydro-1,3-dioxo-2H-isoindol-2-yl)ethyl]-N-phenyl-1H-indole-5-sulphonamide as a foam (4.8 g). The foam was suspended in ethanol (100 ml) containing hydrazine hydrate (5 ml), heated at reflux for 2 h, cooled, the ethanol removed in vacuo and the residue partitioned between sodium carbonate (2 N, 150 ml) and ethyl acetate (2×150 ml). The combined organic extracts were dried (Na$_2$SO$_4$) and evaporated in vacuo to give a foam which was purified by flash chromatography eluted with dichloromethane:ethanol:ammonium hydroxide (20:5:0.2) to give the title compound free base (0.57 g) as a solid. The free base was dissolved in a solution of maleic acid (0.21 g) in methanol (10 ml), and the salt precipitated by the addiion of ethyl acetate (100 ml) and dry ether (300 ml). The salt was filtered off and dried in vacuo to give the title compound as a solid. (0.55 g) m.p. 145°–147°.
Assay Found: C,54.9;H,4.8;N,9.4; C$_{16}$H$_{17}$N$_3$O$_2$S·C$_4$H$_4$O$_4$·0.25H$_2$O requires: C,55.1;H,4,9;N,9.6%.

EXAMPLE 6

N-(4-Ethoxyphenyl)-3-[2-methylamino)ethyl]-1H-indole-5-sulphonamide hydroxhloride hydrate (i) Phenylmethyl [2-[5-[[(4-ethoxyphenyl)amino]sulphonyl]-1H-indol-3-yl]ethyl]carbamate Benzyl chloroformate (1.55 ml) was added portionwise to a stirred solution of the product of Example 4 (4.3 g) in a mixture of ethyl acetate (100 ml) and sodium carbonate (2 N, 100 ml) and the resulting mixture stirred at room temperature for 1 h. The aqueous layer was extracted with ethyl acetate (100 ml), the organic extracts combined, washed with hydrochloric acid (1 N, 100 ml), sodium carbonate (2 N, 100 ml) dried (MgSO$_4$) and evaporated in vacuo to give an oil. The oil was purified by flash chromatography eluted with chloroform:methanol (19:1) to give the title compound as a foam which collapsed to a gum (2.4 g) T.l.c. Silica, Chloroform-methanol (19:1) det. u.v.+Ce$^{IV}$Rf 0.34

(ii)
N-(4-Ethoxyphenyl)-3-[2-(methylamino)ethyl]-1H-indole-5-sulphonamide hydrochloride hydrate A solution of the product of stage (i) (0.5 g) in dry tetrahydrofuran (10 ml) was added dropwise, under nitrogen to a stirred suspension of lithium aluminium hydride (0.2 g) in dry tetrahydrofuran (20 ml). When the addition was complete, the resulting suspension was heated at reflux for 1 h, cooled in ice, and excess reducing agent decomposed by cautious addition of 10% aqueous tetrahydrofuran. Brine (50 ml) and ethyl acetate (50 ml) were added, the mixture filtered and the aqueous layer extracted with ethyl acetate (2×20 ml). The combined extracts were dried (Na$_2$SO$_4$) and evaporated in vacuo to give an oil which was purified by flash chromatography eluted with dichloromethane:ethanol:ammonium hydroxide (50:25:1) to give the title compound free base as an oil. The oil was dissolved in absolute ethanol (10 ml) acidified with ethanolic hydrogen chloride, and the salt precipitated by addition of excess dry ether (200 ml). The salt was filtered off, and dried in vacuo at 60° overnight to give the title compound as a solid (0.19 g) m.p. 116°–120°.
Assay Found: C,53.65;H,5.8;N,9.6; C$_{19}$H$_{23}$N$_3$O$_3$S·HCl. H$_2$O requires C,53.3;H,6.1;N,9.8%

EXAMPLE 7

N-(4-Ethoxyphenyl)-3-[2-(ethylamino)ethyl]-1H-indole-5-suphonamide hydrochloride hydrate (i)
N-[2-[5-[[(4-Ethoxyphenyl)amino]sulphonyl]-1H-indol-3-yl]ethyl]acetamide Acetyl chloride (0.6 ml) was added dropwise to a stirred solution of the product of Example 4 (3.1 g) in dry dimethylformamide (20 ml) containing triethylamine (3.3 ml) and the resulting suspension stirred at room temperature for 30 min. The suspension was partitioned between hydrochloric acid (2 N, 100 ml) and ethyl acetate (2×100 ml) and the combined extracts were washed with sodium carbonate (2 N, 100 ml) dried (MgSO$_4$) and evaporated in vacuo to give an oil. The oil was purified by flash chromatography eluted with chloroform:methanol (19:1) to give the title compound as a foam (0.8 g), a sample of which (0.4 g) was crystallised from a mixture of ethyl acetate and hexane to give the title compound as a crystalline solid (0.3 g) m.p. 173°–175°.

(ii)
N-(4-Ethoxyphenyl)-3-[2-(ethylamino)ethyl]-1H-indole-5-sulphonamide hydrochloride A solution of the product of stage (i) (0.4 g) in tetrahydrofuran (10 ml) was added dropwise, under nitrogen, to a stirred suspension of lithium aluminium hydride (0.4 g) in tetrahydrofuran (20 ml) and the resulting suspension stirred at reflux for 18 h. The suspension was cooled, and excess reducing agent decomposed by cautious addition of 10% aaueous tetrahydrofuran. The mixture was partitioned between sodium carbonate (2 N, 50 ml) and ethyl acetate (2×50 ml) and the combined extracts were dried (Na$_2$SO$_4$) and evaporated in vacuo to give an oil. The oil was purified by flash chromatography eluted with dichloromethane:ethanol:ammonia (50:8:1) to give the title compound free base as oil (about 0.15 g). The free base was dissolved in absolute ethanol (2 ml) acidified with ethereal hydrogen chloride, and the salt precipitated by the addition of excess dry ether (about 100 ml). The salt was filtered off, and dried in vacuo to give the title compound as a solid (0.15 g) m.p. 107°–110°.
Analysis Found: C,55.4;H,6.0;N9.4. C$_{20}$H$_{25}$N$_3$O$_3$S·HCl.0.5H$_2$O requires C,55.5;H,6.3;N,9.7%.

EXAMPLE 8

3-[2-(Dimethylamino)ethyl]-N-(4-ethoxyphenyl)-1H-indole-5-sulphonamide hydrochloride hydrate (i) Phenylmethyl methyl[2-[5-[[(4-ethoxyphenyl)amino]sulphonyl]-1H-indol-3-yl]ethyl]carbamate Benzyl chloroformate (1.0 ml) was added dropwise to a stirred solution of the product of Example 6 (2.6 g) in dimethylformamide (25 ml) containing triethylamine (2.0 ml) and the resulting suspension stirred at room temperature for 15 min. The suspension was partitioned between 2 N hydrochloric acid (100 ml) and ethyl acetate (2×100 ml). The combined extracts were washed with 2 N sodium carbonate (100 ml), water (100 ml) dried (Na$_2$SO$_4$) and evaporated in vacuo to give an oil which was purified by flash chromatography eluted with cloroform methanol (50:1) (Rf 0.23) to give the title compound as a foam (1.4 g). A sample (0.5 g) was further purified by flash chromatography eluted with hexane-ethyl acetate (1:1) to give pure title compound as a gum, which crystallised on standing.

(ii) 3-[2-(Dimethylamino)ethyl]-N-(4-ethoxyphenyl)-1H-indole-5-sulphonamide hydrochloride A solution of the product of stage (i) (0.9 g) in tetrahydrofuran (15 ml) was added dropwise, under nitrogen, to a stirred suspension of lithium aluminium hydride (0.5 g) in tetrahydrofuran (10 ml) and the resulting mixture heated at reflux for 16 h. The mixture was cooled and excess reducing agent decomposed by cautious addition of 10% aqueous tetrahydrofuran. The resulting mixture was partitioned betweeen sodium carbonate (2 N, 75 ml) and ethyl acetate (2×50 ml) and the combined extracts were dried (Na$_2$SO$_4$) and evaporated in vacuo to give the title compound free base as an oil. The oil was dissolved in absolute ethanol (10 ml) acidified with ethereal hydrogen chloride and the salt precipitated by addition of excess dry ether (150 ml). the salt was filtered off, and dried in vacuo to give the title compound as a solid (0.42 g), m.p. 119°–121°.

T.l.c. Silica:Dichloromethane-ethanol-aqueous ammonia solution (50:8:1) det u.v.+IPA Rf=0.3 Analysis Found: C,54.4;H,6.2;N,9.3. C$_{20}$H$_{25}$N$_3$O$_3$S.HCl.H$_2$O requires C,54.3;H,6.4;N,9.5%.

The following example illustrates a pharmaceutical formulation according to the invention containing N-(4-Ethoxyphenyl)-3-[2-(methylamino)ethyl]-1H-indole-5-sulphonamide hydrochloride hydrate as the active ingredient. Other compounds of the invention may be formulated in a similar manner.

| Tablets for Oral Administration | mg/tablet |
|---|---|
| Active ingredient | 10 |
| Magnesium stearate BP | 0.5 |
| Anhydrous Lactose | 99 |

The active ingredient is sieved and blended with the anhydrous lactose and magnesium stearate. The mix is then compressed into tablets using a Manesty F$_3$ tablet machine fitted with 8.0 mm concave punches.

We claim:

1. A method of treating a patient suffering from or susceptable to migrane which comprises administering to the patient an effective amount of a compound having a formula (I)

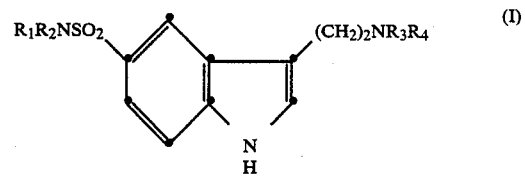

wherein

R$_1$ represents a hydrogen atom, A C$_{1-6}$ alkyl or C$_{3-6}$ alkenyl group; R$_2$ represents a hydrogen atom, C$_{1-3}$ alkyl, C$_{3-6}$ alkenyl, C$_{5-7}$ cycloalkyl, phenyl, phen(C$_{1-4}$) alkyl in which the phenyl ring alone or as part of phen(C$_{1-4}$)alkyl is unsubstituted or substituted b a halogen atom, C$_{1-3}$ alkyl, C$_{1-3}$ alkoxy, hydroxyl, or by a group NR$^a$R$^b$, or CONR$^a$R$^b$, wherein R$^a$ and R$^b$, which may be the same or different, each represents a hydrogen atom or C$_{1-3}$ alkyl; R$_3$ and R$_4$, which may be the same or different each represents a hydrogen atom, C$_{1-3}$ alkyl or 2-propenyl; or a physiologically acceptable salt or hydrate thereof.

2. A method of treating a patient suffering from the susceptable to migraine which comprises administering to the patient an effective amount of a pharmaceutical composition comprising at least one compound having a formula (I)

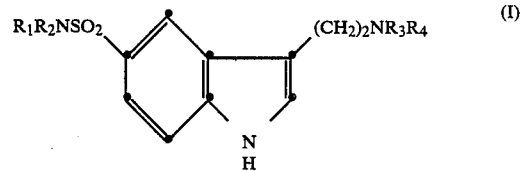

wherein

R$_1$ represents a hydrogen atom, a C$_{1-6}$ alkyl or C$_{3-6}$ alkenyl group; R$_2$ represents a hydrogen atom, C$_{1-3}$ alkyl, C$_{3-6}$ alkenyl, C$_{5-7}$ cycloalkyl, phenyl, phen(C$_{1-4}$)alkyl in which the phenyl ring alone or as part of phen(C$_{1-4}$)alkyl is unsubstituted or substituted by a halogen atom, C$_{1-3}$ alkyl, C$_{1-3}$ alkoxy, hydroxyl group, or by a grou NR$^a$R$^b$, or CONR$^a$R$^b$, wherein R$^a$ and R$^b$, which may be the same or different, each represents a hydrogen atom or C$_{1-3}$ alkyl; R$_3$ and R$_4$, which may be the same or different each represents a hydrogen atom, C$_{1-3}$ alkyl or 2-propenyl; or a physiologically acceptable salt or hydrate thereof, together with at least one physiologically acceptable carrier or excipient.

* * * * *